United States Patent
Stryker et al.

(10) Patent No.: US 6,670,512 B2
(45) Date of Patent: Dec. 30, 2003

(54) SUBSTITUTED TETRAARYLETHYLENE COMPOUNDS

(76) Inventors: Jeffrey Mark Stryker, 8726-120 Street, Edmonton, Alberta (CA), T6G 1X3; Udo Hendrick Verkerk, #407, 11012-82 Avenue, Edmonton, Alberta (CA), T6G 2P6; Megumi Fujita, #1616, 8515-112 Street, Edmonton, Alberta (CA), T6G 1K7; Makoto Yasuda, 602H Michener Park, Edmonton, Alberta (CA), T6H 5A1

( * ) Notice: Subject to any disclaimer, the term of this patent is extended or adjusted under 35 U.S.C. 154(b) by 0 days.

(21) Appl. No.: 10/177,404

(22) Filed: Jun. 21, 2002

(65) Prior Publication Data

US 2002/0183540 A1 Dec. 5, 2002

Related U.S. Application Data

(62) Division of application No. 09/336,388, filed on Jun. 18, 1999, now abandoned.

(51) Int. Cl.$^7$ ................................ C07C 39/12
(52) U.S. Cl. ................ 568/720; 568/723; 568/640; 568/646; 560/140; 560/144; 560/146; 562/87; 562/88; 562/89; 562/115
(58) Field of Search ................ 568/720, 723, 568/640, 646; 562/87, 88, 89, 115; 560/140, 144, 146

(56) References Cited

U.S. PATENT DOCUMENTS 4,092,306 A  * 5/1978 Eastlick .................. 534/560
5,587,464 A  * 12/1996 Kawahara et al. ........ 534/558

OTHER PUBLICATIONS

Bethell et al., J. Chem. Soc., Aug. 1963, pp. 3808–3819.*
Chemische Berichte, 1872, 5, 277–278.
Kogyo Kagaku Zasshi, 61, 481–2 (1958).
J. Org. Chem, 1962, 27, 1597–1601 "Oxidation with Nickel Peroxide", Nakagawa et al.
Tetrahedron Letters, No. 35, p. 4153–4159 1966 Boron Trienloride as Selective Demethylating Agent Dean et al.

* cited by examiner

*Primary Examiner*—Rosalynd Keys
(74) *Attorney, Agent, or Firm*—Kenneth H. Johnson

(57) ABSTRACT

The present invention seeks to provide novel tetraarylethylene compounds which are substituted on the aryl rings ortho to the ethylenic carbon atoms and processes for the preparation for such compounds. The compounds have potential use as molecular templates.

12 Claims, No Drawings

SUBSTITUTED TETRAARYLETHYLENE COMPOUNDS

This is a continuation of application Ser. No. 09/336,388, filed Jun. 18, 1999, now abandoned.

FIELD OF THE INVENTION

The present invention relates to tetraarylethylene compounds. More particularly the present invention relates to substituted tetraaryl compounds, preferably which contain functional groups, most preferably terminal functional groups. Such compounds have the potential to act as molecular "templates" for metal complexation. That is, for example, a tetraaryl ethylene compound having at least one, preferably at least two functional substituents on either side of the plane defined by the sigma bonds attached to the ethylenic carbon atoms could form a "supramolecular assembly" comprising alternating layers of a metal atom and the tetraaryl compound.

BACKGROUND OF THE INVENTION

Chemische Berichte, 1872, 5, 278 reports work by A. Behr to make a substituted tetraphenylethylene. The compound was manufactured from benzophenone and the resulting compounds are hydroxyl substituted in the aromatic (aryl) ring para to the ethylenic carbon atoms. There are a number of subsequent references to this paper, including Kogyo Kagaku Zasshi, 61, 481–2 (1958) by Yoshiro Nakamura, which clearly establishes that the oxidation and subsequent alkylation is para to the ethylenic carbon atoms. The reference fails to clearly teach ortho substituted tetraarylethylenes. Further, the references also fail to teach tetraarylethylene which is substituted both above and below the plane defined by the sigma bonds attached to the ethylenic carbon atoms.

Accordingly, the present invention seeks to provide novel tetraarylethylene compounds.

SUMMARY OF THE INVENTION

The present invention provides a compound of formula I:

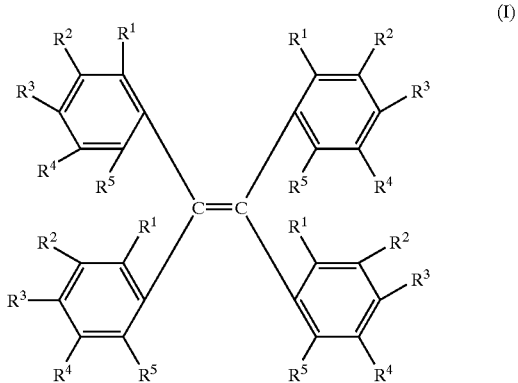

(I)

wherein at least two $R^1$ are the same and not a hydrogen atom; and $R^1$, $R^2$, $R^3$, $R^4$ and $R^5$ are independently selected from the group consisting of a hydrogen atom; a halogen atom; a hydroxyl radical; a $C_{1-20}$ alkyl radical which is unsubstituted or substituted by one or more substituents selected from the group consisting of a halogen atom, a hydroxyl radical or a carboxyl radical; a $C_{3-20}$ allyl radical; a $C_{1-20}$ alkoxy radical which is unsubstituted or substituted by one or more substituents selected from the group consisting of a halogen atom, a hydroxyl radical or a carboxyl radical; a $C_{3-20}$ allyloxy radical; a carbalkoxy radical of the formula —COOR$^{20}$ wherein R$^{20}$ is a hydrogen atom or a $C_{1-20}$ alkyl radical which is unsubstituted or substituted by one or more substituents selected from the group consisting of a halogen atom, a hydroxyl radical or a carboxyl radical; a carboxylate radical of the formula —OCOR$^{30}$ wherein R$^{30}$ is a $C_{1-20}$ alkyl radical which is unsubstituted or substituted by one or more substituents selected from the group consisting of a halogen atom, a hydroxyl radical or a carboxyl radical; a $C_{6-10}$ aryl radical which is unsubstituted or substituted by one or more substituents selected from the group consisting of a halogen atom, a hydroxyl radical or a carboxyl radical; a $C_{6-10}$ aryloxy radical or a $C_{7-11}$ benzyloxy radical which is unsubstituted or substituted by one or more substituents selected from the group consisting of a halogen atom, a hydroxyl radical or a carboxyl radical; an acyl R$^6$CO— radical wherein R$^6$ is a $C_{1-20}$ alkyl radical which is unsubstituted or substituted by one or more substituents selected from the group consisting of a halogen atom, a hydroxyl radical or a carboxyl radical; an amido radical which is unsubstituted or substituted by up to two $C_{1-20}$ alkyl radicals; a (—O—)$_n$—P(R$^7$)$_2$ radical wherein each R$^7$ is independently selected from the group consisting of a $C_{1-20}$ alkyl radical, a $C_{1-20}$ alkoxy radical, a $C_{6-10}$ aryl radical and n is 0 or 1; a (—O—)$_n$—PO(R$^8$)$_2$ radical wherein each R$^8$ is independently selected from the group consisting of a $C_{1-20}$ alkyl radical, a $C_{1-20}$ alkoxy radical, a $C_{6-10}$ aryl radical and n is 0 or 1; a —Si(R$^9$)$_3$ radical wherein each R$^9$ is independently selected from the group consisting of a $C_{1-20}$ alkyl radical, a $C_{6-10}$ aryl radical, a hydrogen radical and an alkoxy radical; a trifluormethanesulfonyloxy radical; or two or more of adjacent substituents R$^2$, R$^3$, R$^4$ and R$^5$ may be taken together to form a fused ring.

The present invention also provides a process for the preparation of a 2,2',2",2'''-(tetra $C_{1-6}$ alkoxy) tetraphenylethylene comprising acid catalyzed decomposition of the diazo derivative of 2,2'-di $C_{1-6}$ alkoxybenzophenone hydrazone at a temperature of less than 25° C. in the absence of light.

The present invention also seeks to provide a process for the preparation of 2,2',2",2''',6,6',6",6'''-octa $C_{1-4}$ alkoxy tetraphenylethylene comprising the controlled oxidation of 1,1,2,2,-tetrakis(2',6'-di $C_{1-6}$ alkoxyphenyl)ethane. Typically the oxidation takes place in the presence of triphenylmethyl hexafluorophosphate in an inert solvent at low temperatures typically from about 0° C. to about 25° C. It is believed that the resulting 2,2',2",2''',6,6',6",6'''-octa $C_{1-6}$ alkoxy tetraphenylethylene compound may be dealkylated to 2,2',2",2''',6,6',6",6'''-octahydroxy tetraphenylethylene.

In a further embodiment the present invention provides a process for the preparation of 1,1,2,2-tetrakis(2',6'-di $C_{1-6}$ alkoxyphenyl)ethane comprising the radical coupling of bis(2,6-di $C_{1-6}$ alkoxyphenyl)methanol and bis(2,6-di $C_{1-4}$ alkoxyphenyl)methane in equimolar amounts in an inert solvent in the presence of p-toluene sulphonic acid.

A second method of preparation of 1,1,2,2-tetrakis(2',6'-di $C_{1-6}$ alkoxyphenyl)ethane is provided by the reductive radical coupling of bis(2,6-di $C_{1-6}$ alkoxyphenyl)methanol using chromous ion (CrCl$_2$) in an acidic medium (HCl).

A further aspect of the present invention provides a process for the synthesis of unsymmetrically substituted tetraphenylethylene compounds of formula 1 wherein two $R^1$ substituents on opposite ends of the central ethylene moiety are $C_{1-20}$ alkoxy radicals (as defined above) and two $R^1$ substituents on opposite ends of the central ethylene moiety are benzyloxy radicals (as defined above) comprising acid catalyzed decomposition of the diazo derivative of 2-$C_{7-11}$ benzyloxy, 2'-$C_{1-20}$ alkoxy benzophenone.

In the diazo-coupling reaction of 2-benzyloxy-2'-methoxybenzophenone hydrazone to give the dibenzyloxydimethoxytetraphenylethylene, both double bond isomers are produced, giving a mixture of E and Z—1,2-di(2'-benzyloxyphenyl)-1,2-di(2'-methoxyphenyl)ethane. The subsequent hydrogen resulted in the separable E and Z—1,2-di(2'-hydroxyphenyl)-1,2-di(2'-methoxyphenyl)ethylene.

In a further aspect of the present invention the resulting unsymmetrically substituted tetraphenylethylene compounds of formula I wherein two $R^1$ substituents on opposite ends of the central ethylene moiety are $C_{1-20}$ alkoxy radicals (as defined above) and two $R^1$ substituents on opposite ends of the central ethylene moiety are $C_{7-11}$ benzyloxy radicals (as defined above) may be subjected to catalytic hydrogenolysis (hydrogenation) to convert the benzyloxy radicals to hydroxyl radicals. Preferably the catalyst is palladium on carbon. Both E and Z isomers can be produced in this way and either separated and used individually or used as a mixture.

In a further embodiment the present invention provides a process for producing compounds of formula I above wherein all $R^1$ substituents are $C_{3-20}$ allyloxy radicals comprising reacting the compounds of formula I above wherein all $R^1$ substituents are hydroxyl radicals with excess 1-halo $C_{3-20}$ allyl compound. Preferably the halo substituent is a bromine atom. The resulting compound may be subject to a high temperature Claisen rearrangement to yield the compounds of formula I wherein all $R^1$ substituents are hydroxy radicals and all $R^2$ substituents are $C_{3-20}$ allyl radicals. The resulting compounds may then be catalytically hydrogenated so that the allyl substituents ($R^2$) are hydrogenated to the corresponding alkane substituents.

DETAILED DESCRIPTION

In the compounds of the present invention preferably $R^1$, $R^2$, $R^3$, $R^4$ and $R^5$ are independently selected from the group consisting of a hydrogen atom; a halogen atom; a hydroxyl radical; a $C_{1-6}$ alkyl radical which is unsubstituted or substituted by one or more substituents selected from the group consisting of a halogen atom, a hydroxyl radical or a carboxyl radical; a $C_{3-6}$ allyl radical; a $C_{1-6}$ alkoxy radical which is unsubstituted or substituted by one or more substituents selected from the group consisting of a halogen atom, a hydroxyl radical or a carboxyl radical; a $C_{3-6}$ allyloxy radical; a carbalkoxy radical of the formula —$COOR^{20}$ wherein $R^{20}$ is a hydrogen atom or a $C_{1-6}$ alkyl radical which is unsubstituted or substituted by one or more substituents selected from the group consisting of a halogen atom, a hydroxyl radical or a carboxyl radical; a carboxylate radical of the formula —OC—$OR^{30}$ wherein $R^{30}$ is a $C_{1-6}$ alkyl radical which is unsubstituted or substituted by one or more substituents selected from the group consisting of a halogen atom, a hydroxyl atom or a carboxyl atom; a $C_{6-10}$ aryl radical which is unsubstituted or substituted by one or more substituents selected from the group consisting of a halogen atom, a hydroxyl radical or a carboxyl radical; a $C_{6-10}$ aryloxy radical or a $C_{7-11}$ benzyloxy radical which may be unsubstituted or substituted by one or more substituents selected from the group consisting of a halogen atom, a hydroxyl radical or a carboxyl radical; an acyl $R^6CO$— radical wherein $R^6$ is a $C_{1-6}$ alkyl radical which is unsubstituted or substituted by one or more substituents selected from the group consisting of a halogen atom, a hydroxyl radical or a carboxyl radical; an amido radical which is unsubstituted or substituted by up to two $C_{1-6}$ alkyl radicals; a (—O—)$_n$—P($R^7$)$_2$ radical wherein each $R^7$ is independently selected from the group consisting of a $C_{1-6}$ alkyl radical, a $C_{1-6}$ alkoxy radical, a $C_{6-10}$ aryl radical and n is 0 or 1; a (—O—)$_n$—PO($R^8$)$_2$ radical wherein each $R^8$ is independently selected from the group consisting of a $C_{1-6}$ alkyl radical, a $C_{1-6}$ alkoxy radical, a $C_{6-10}$ aryl radical and n is 0 or 1; a —Si($R^9$)$_3$ radical wherein each $R^9$ is independently selected from the group consisting of a $C_{1-6}$ alkyl radical and a $C_{6-10}$ aryl radical; and a trifluorosulfonyloxy radical. Preferably $R^2$, $R^3$ and $R^4$ are selected from the group consisting of a hydrogen atom or a lower $C_{1-4}$ alkyl radical, most preferably a hydrogen atom.

In a particularly preferred embodiment of the present invention, preferably at least two, more preferably up to four of the $R^1$ substituents are independently selected from the group consisting of hydroxyl radicals; alkoxy radicals; aryloxy radicals; carboxyl radical; a (—O—)$_n$—P($R^7$)$_2$ radical wherein each $R^7$ is independently selected from the group consisting of a $C_{1-6}$ alkyl radical, a $C_{1-6}$ alkoxy radical, a $C_{6-10}$ aryl radical and n is 0 or 1; and a trifluorosulfonyloxy radical. In a further preferred embodiment of the present invention at least two, most preferably up to four of the $R^1$ and at least two, most preferably up to four, of the $R^5$ radicals are independently selected from the group consisting of hydroxyl radicals; alkoxy, preferably $C_{1-6}$ radicals; a (—O—)$_n$—P($R^7$)$_2$ radical wherein each $R^7$ is independently selected from the group consisting of a $C_{1-6}$ alkyl radical, a $C_{1-6}$ alkoxy radical, a $C_{6-10}$ aryl radical and n is 0 or 1; and aryloxy, preferably $C_{6-10}$ radicals; and a trifluoromethanesulfonyloxy radical. Preferably at least two and most preferably all four $R^1$ subsitituents are the same. Preferably at least two and most preferably all four $R^5$ substituents are the same. In a further aspect of the present invention all the $R^1$ substituents are the same and all the $R^5$ substituents are the same. In the above embodiments $R^1$ and $R^5$ are as described above.

Some of the compounds of the present invention may be prepared by the acid catalyzed decomposition of a diazo compound of formula II:

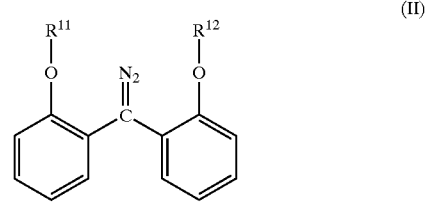

(II)

wherein $R^{11}$ and $R^{12}$ are independently selected from the group consisting of a $C_{1-6}$ alkyl radical and a $C_{6-10}$ aryl radical, preferably a $C_{1-4}$ alkyl radical or a benzyl radical.

In one embodiment of the present invention, $R^{11}$ and $R^{12}$ are the same and are $C_{1-6}$, most preferably $C_{1-4}$ alkyl radicals, preferably methyl radicals (a symmetrically substituted compound). In another embodiment of the invention, $R^{11}$ is a $C_{1-6}$, most preferably a $C_{1-4}$ alkyl radical, preferably a methyl radical; and $R^{12}$ is a $C_{6-10}$ benzylic radical, preferably benzyl (i.e. an unsymmetrically substituted compound).

A suitable acid is anhydrous p-toluene sulphonic acid. The reaction is carried out at low temperatures, typically less than 25° C., in the absence of light or heat. In the case where $R^{11}$ and $R^{12}$ are the same and an alkyl radical, the resulting product is 2,2',2",2'"-(tetraalkoxy)tetraphenylethylene. Preferably, the alkyl substituent is a $C_{1-4}$ alkyl radical, most preferably methyl. In the case where R¹¹ is an alkyl radical and R¹² is a benzyl radical, the resulting product is a mixture of E and Z—1,2-di(2'-benzyloxyphenyl)-1,2-di(2'-methoxyphenyl)ethylene.

In a further embodiment of the invention the mixture of unsymmetrically substituted E and Z—1,2-di(2'-benzyloxyphenyl)-1,2-di(2'-methoxyphenyl)ethylene compounds may further be catalytically hydrogenolyzed at the benzyloxy substituents to produce separable E and Z—1,2-di(2'-hydroxyphenyl)-1,2-di(2'-methoxyphenyl)ethylene compounds (i.e. the compounds of formula I wherein two R¹ substituents at opposite ends of the central ethylene moiety are hydroxyl radicals and two R¹ substituents at opposite ends of the central ethylene moiety are methoxy radicals).

The hydrogenolysis may be carried out in the presence of hydrogen under moderate pressure, from about 100 to 1000, preferably from about 300 to 600 psi (689.5×10³ Pa to 6.895×10³ kPa, preferably from about 2.068×10³ kPa to 20.685×10³ kPa).

The diazo starting material may be prepared by the oxidation of a compound of formula III:

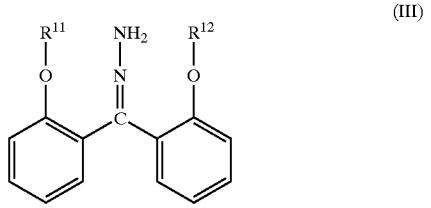

(III)

wherein R¹¹ and R¹² are as defined in formula II. If R¹¹ and R¹² are the same and a $C_{1-6}$ alkyl radical, the compound (formula III), is a 2,2'-$C_{1-6}$ alkoxybenzophenone hydrazone or a 2,2'-$C_{1-6}$ alkoxy benzhydrylidene-hydrazine. If R¹¹ is a $C_{1-6}$ alkoxy radical and R¹² is a benzyl radical the compound is a 2-benzyloxy-2'-alkoxybenzophenone hydrazone or a 2-benzyloxy-2'-alkoxybenzhydrylidene-hydrazine. As noted above, preferably the alkyl radical is a methyl radical and if present the benzyl radical is unsubstituted. Preferred starting materials are 2,2'-dimethoxybenzophenone hydrazone or 2,2'-dimethoxybenzhydrylidene-hydrazine, and 2-benzyloxy-2-methoxybenzophenone hydrazone or 2-benzyloxy-2-methoxybenzhydrylidene-hydrazine.

The oxidation may be carried out in the present of nickel peroxide. Care must be taken with this oxidation. The reaction should be carried out at low temperatures, preferably 0° C. or less (e.g. an ice-salt bath) and the reaction should be protected from light which will decompose the diazo product.

The compound of formula III may be prepared by the reaction of a compound of formula IV:

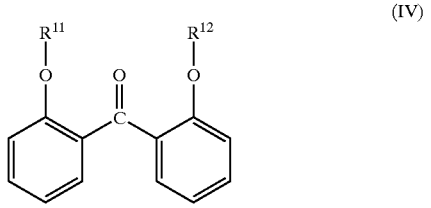

(IV)

wherein R¹¹ and R¹² are as defined above with hydrazine monohydrate (at high temperature).

For the symmetrically substituted compounds the starting 2,2'-dialkoxy benzophenone may be prepared by metallation of anisole with n-butyllithium in a suitable solvent such as diethylether/tetramethylethylenediamine and subsequent quenching with N,N-dimethylcarbamoyl chloride or by methylation of commercially available 2,2'-dihydroxybenzophenone using excess methyl iodide and sodium hydroxide in a highly polar organic solvent (e.g. dimethyl sulfoxide (DMSO)).

For the unsymmetrically substituted compounds, the symmetrically substituted alkoxy compound is prepared and one of the alkoxy groups is converted to an unsymmetrically substituted 2-hydroxy-2'-methyloxybenzophenone in the presence of boron trichloride at a temperature from −65° C. to 25° C. The resulting 2-hydroxy-2'-methyloxybenzophenone is then benzylated using benzyl bromide in the presence of potassium carbonate to yield 2-benzyloxy-2'-methoxybenzophenone. Alternative reaction routes would be known or derivable to those skilled in the art.

Once the 2,2',2",2'''-(tetraalkoxy)tetraphenylethylene is prepared, the alkoxy groups may be de-alkylated to the tetra hydroxyl derivative. For example, 2,2',2",2'''-(tetramethoxy) tetraphenylethylene may be demethylated using boron tribromide at low temperatures to produce the tetra hydroxyl derivative. Additionally, the 2,2',2",2'''-(tetrahydroxy) tetraphenylethylene may be further treated, for example, with compounds such as anhydrides of $C_{1-6}$ carboxylic acids such as acetic anhydride in pyridine to produce 2,2',2",2'''-(tetraacetoxy)tetraphenylethylene and with trifluoromethanesulfonic anhydride to produce 2,2',2",2'''-tetrakis(trifluorosulfonyloxy)tetraphenylethylene.

The 2,2',2",2'''-(tetrahydroxy)tetraphenylethylene may also be reacted with a $C_{3-20}$, preferably a $C_{3-6}$ allylating agent such as a 1-halo $C_{3-20}$, preferably a $C_{3-6}$ allyl compound. The resulting 2,2',2",2'''-tetra $C_{3-20}$, preferably $C_{3-6}$ allyloxy tetraphenylethylene may then be heated to cause a Claisen rearrangement resulting in a 2,2',2",2'''-tetrahydroxy-3,3',3",3'''-tetra $C_{3-20}$, preferably $C_{3-6}$ allyl tetraphenylethylene which may then be hydrogenated as described above to yield a 2,2',2",2'''-tetrahydroxy-3,3',3", 3'''-tetra $C_{3-30}$, preferably $C_{3-6}$ alkyl tetraphenylethylene. The simplest allylating agent is allylbromide (1-bromo-2-propene) yielding sequentially as described above 2,2',2", 2'''-tetra(allyloxy)tetraphenylethylene (or 2,2',2",2'''-tetra(2-propenyloxy)tetraphenylethylene); 2,2',2",2'''-tetrahydroxy-3,3',3",3'''-tetra(allyl)tetraphenylethylene (or 2,2',2",2'''-tetrahydroxy-3,3',3",3'''-tetra(2-propenyl) tetraphenylethylene); and 2,2',2",2'''-tetrahydroxy-3,3',3", 3'''-tetra(n-propyl)tetraphenylethylene, respectively.

Other reaction schemes and methods of altering the substituents are well known to those skilled in the art. For example, the hydroxy derivative could be esterified using common acid chlorides and anhydrides or phospharylated using common chlorophosphines (ClPR"₂) or chlorophosphates (ClP(O)R"₂). Further, the trifluorosulphenylate derivative may be transformed using palladium catalyzed substitution using appropriate carbon, nitrogen, phosphorus and oxygen nucleaphiles.

In a further embodiment of the present invention the 2,2',2",2''',6,6',6",6'''-octa $C_{1-6}$ alkoxy tetraphenylethylene (also tetrakis(2,6-di $C_{1-6}$ alkoxyphenyl)ethylene) compound may be prepared by the controlled oxidation of a compound of formula V:

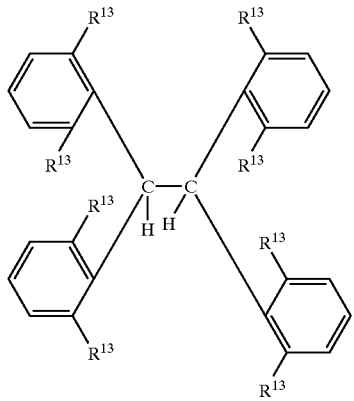

(2,2',2'',2''',6,6',6'',6'''-octa $C_{1-6}$ alkoxy tetraphenylethane (also tetrakis(2,6-di $C_{1-6}$ alkoxyphenyl)ethane) wherein $R^{13}$ is a $C_{1-6}$, preferably a $C_{1-4}$ alkoxy radical, most preferably methoxy or ethoxy. Most preferably all $R^{13}$ radicals are the same. One method for the controlled oxidation of the compound is by reaction with triphenylmethylhexafluorophosphate in an inert solvent such as dichloromethane. The reaction may be carried out at temperatures from 0° C. to 25° C.

The resulting 2,2',2'',2''',6,6',6'',6'''-octa $C_{1-6}$ alkoxy tetraphenylethylene (also tetrakis(2,6-di $C_{1-6}$ alkoxyphenyl) ethylene) compounds may then be subjected to dealkylation to yield 2,2',2'',2''',6,6',6'',6'''-octahydroxyphenylethylene. The dealkylation has been described above. One method for dealkylation is to treat the 2,2',2'',2''',6,6',6'',6'''-octa $C_{1-6}$ alkoxy tetraphenylethylene (also tetrakis(2,6-di $C_{1-6}$ alkoxyphenyl)ethylene) compound with boron tribromide at temperatures from 0° C. to 25° C.

The resulting 2,2',2'',2''',6,6',6'',6'''-octahydroxyphenylethylene compound may be treated as described above (for example acetoxylation or allylated and subsequently subjected to a rearrangement reaction) to yield further derivatives as described above.

The compounds of formula V (2,2',2'',2''',6,6',6'',6'''-octa $C_{1-6}$ alkoxy tetraphenylethane (also tetrakis(2,6-di $C_{1-6}$ alkoxyphenyl)ethane) may be prepared by the radical coupling of a compound of formula VI:

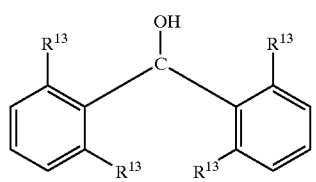

(bis(2,6-di $C_{1-6}$ alkoxyphenyl)methanol) wherein $R^{13}$ is as defined above with a compound of formula VII:

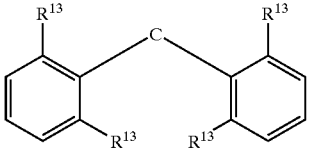

(bis(2,6-di $C_{1-4}$ alkoxyphenyl)methane) wherein $R^{13}$ is as defined above, in an inert solvent in the presence of p-toluene sulphonic acid.

A second method for generation of 1,1,2,2-tetrakis(2',6'-di $C_{1-6}$ alkoxyphenyl)ethane is by the reductive radical dimerization of compound (VI) using chromous chloride and hydrochloric acid in acetone solution. The products of these two coupling methods are rotational isomers, each with distinct chemical reactivity.

The compounds of formula VI may be prepared by metallation of a compound of formula VIII:

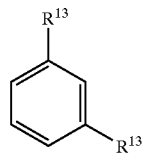

wherein $R^{13}$ is as defined above with n-butyllithium in an inert solvent, preferably diethyl ether/tetramethylenediamine solution, followed by quenching with ethyl formate.

The compounds of formula VII above may be prepared by reducing the compounds of formula VI above for example by treatment with stoichometric amounts of p-toluenesulfonic acid in a mixture of acetonitrile and tetrahydrofuran.

The present invention will now be illustrated by the following non-limiting examples in which unless otherwise indicated parts means parts by weight (e.g. grams) and per cent means weight per cent.

STARTING HYDRAZONE

A stirred suspension of 2,2'-dimethoxybenzophenone (20.72 g, 0.0855 mol) and 20 mL (0.412 mol) of hydrazine monohydrate in 25 mL of 1-butanol was heated to reflux overnight. After cooling to room temperature the two phase reaction mixture was poured into water and cooled to induce crystallization. The white precipitate was filtered, washed with water and petroleum ether and dried in vacuo to yield 2,2'-dimethoxybenzophenone hydrazone (1).

EXAMPLE 1

2,2',2'',2'''-(tetramethoxy)tetraphenylethylene

To a solution of 1 (5.12 g, 0.020 mol) in 200 mL of anhydrous acetonitrile cooled to 0° C. and protected from light was added in one portion and excess of nickel peroxide (12.7 g). The nickel peroxide was prepared as described in J. Org. Chem., 1962, 27, 1597. The mixture was stirred for one hour at 0° C. and then filtered through basic alumina (Activity I) to remove the nickel residues. After rinsing the alumina with acetonitrile the intense pink-red filtrate was cooled to 0° C. and treated with one drop of a benzene solution of p-toluene sulfonic acid (3.6 g of p-toluene sulfonic acid in 39 mL of anhydrous benzene). Over about one hour a white precipitate slowly separates from the light yellow reaction mixture. The precipitate was filtered and washed to yield 2,2',2",2'"-(tetramethoxy) tetraphenylethylene (2).

EXAMPLE 2

Demethylation of 2

A suspension of 2 (0.466 g, 1.03 mmol) in 30 mL of anhydrous dichloromethane cooled to −65° C. was treated with boron tribromide (0.7 mL, 7.04 mmol). The solids dissolved immediately and the purple solution warmed to room temperature and was stirred overnight. The reaction mixture was pored into cold saturated aqueous sodium bicarbonate and diluted with diethyl ether. The organic phase was washed with water and a saturated salt solution, dried over sodium sulfate, concentrated in vacuo and purified by recrystallization from diethyl ether to yield 2,2',2", 2'"-(tetrahydroxy)tetraphenylethylene (3).

EXAMPLE 3

Treatment of 3 with Acetic Anhydride

A suspension of 3 (0.50 g, 0.126 mmol) was treated with 1 mL of acetic anhydride and anhydrous pyridine at room temperature. The solids dissolved within a few minutes and after about 20 minutes the reaction mixture was diluted with 10 mL of dichloromethane and washed successively with water, 1N hydrochloric acid, saturated aqueous bicarbonate and saturated salt. The organic phase was dried over sodium sulfate and the volatiles removed in vacuo to yield the crude product, which was subsequently purified by recrystallization from acetone to yield 2,2',2",2'"-(tetraacetoxy) tetraphenylethylene (4) quantitatively.

EXAMPLE 4

Treatment of 3 with Trifluoromethanesulfonic Anhydride

To a mixture of 3 (4.30 g, 0.018 mmol) and 24 mL of anhydrous pyridine at 0° C. under a nitrogen atmosphere was added dropwise via syringe trifluoromethanesulphonic anhydride (15.5 g, 0.055 mol). The dark brown reaction mixture was warmed to room temperature and was stirred for 24 hours. The reaction was quenched by the addition of 60 mL of water. The crude mixture was repeatedly extracted with diethyl ether and the combined extracts washed sequentially with water, 10% aqueous HCl and saturated salt. The combined aqueous phases were back extracted with several portions of diethyl ether and the combined organic phases were dried over magnesium sulphate, filtered and evaporated to dryness. The yellow residue was purified by recrystallization from acetone or from acetone and acetonitrile to yield 2,2',2",2'"-tetrakis(trifluoromethylsulfonyloxy) tetraphenylethylene (5) quantitatively.

EXAMPLE 5

Preparation of 2,2',2",2'",6,6',6",6'"-octahydroxytetraphenylethylene (6)

A. Bis(2,6-dimethoxyphenyl)methanol (2)

To a solution of 1,3-dimethoxybenzene (19.5 mL, 0.150 mol) in diethyl ether at −78° C. was added n-butyllithium (94 mL of a 1.6 M solution in hexanes) and dried N,N,N', N'-tetramethylethylenediamine (2.25 mL, 0.015 mol). The mixture was warmed gradually to room temperature over 2 hours and then re-cooled to −78° C. Ethyl formate (6.2 mL, 0.075 mol) was added slowly via syringe, after which the solution was warmed to room temperature and stirred for 15 hours. The reaction was quenched by the addition of water (40 mL) and 10% aqueous hydrochloric acid, giving a white solid which was collected by filtration and washed with water and ether to give pure bis(2,6-dimethoxyphenyl) methanol.

B. Bis(2,6-dimethoxyphenyl)methane (3)

To a solution of bis(2,6-dimethoxyphenyl)methanol (4.37 g, 0.014 mol) in acetonitrile (50 mL) and tetrahydrofuran (65 mL) was added p-toluenesulfonic acid monohydrate (2.73 g, 0.014 mol) at 0° C. The resulting solution was warmed to room temperature and stirred for 17 hours, after which water (60 mL) was added and the solvent removed under reduced pressure. The residue was extracted with diethyl ether and the combined extracts dried over anhydrous magnesium sulfate. Removal of the solvent in vacuo gave bis(2,6-dimethoxyphenyl)methane.

C(a). 1,1,2,2-tetrakis(2',6'-dimethoxyphenyl)ethane (4)

To a solution of bis(2,6-dimethoxyphenyl)methanol (1.52 g, 0.005 mol) in acetonitrile (50 mL) at room temperature was added p-toluenesulfonic acid monohydrate (0.95 g, 0.005 mol). To the resulting deep red solution was added bis(2,6-dimethoxyphenyl)methane (1.44 g, 0.005 mol). The reaction mixture decolored within about one hour and was stirred for an additional 17 hours. The reaction was quenched by the addition of water (10 mL), extracted with dichloromethane and dried over anhydrous magnesium sulfate. Evaporation of the solvent and hot filtration using hexane/benzene gave 1,1,2,2-tetrakis(2',6'-dimethoxyphenyl)ethane as a mixture of rotational isomers after evaporation of the solvents and washing with diethyl ether.

C(b). 1,1,2,2-tetrakis(2',6'-dimethoxyphenyl)ethane (4)

To a suspension of commercial $CrCl_2$ (1.69 g, 13.75 mmol) in acetone (25.0 mL) and aqueous HCl (36%,12.5 mL) was added bis(2,6-dimethoxyphenyl)methanol (1.52 g, 5 mol) at 0° C. The resulting mixture was stirred and warmed to room temperature. After 3 hours, water (20 mL) was added and the mixture was extracted with dichloromethane. The combined organic phases were dried over $MgSO_4$ and concentrated to deposit 1,1,2,2-tetrakis(2',6'-dimethoxyphenyl)ethane as a white solid single rotational isomer.

D. Tetrakis(2,6-dimethoxyphenyl)ethylene (5)

To a solution of commercial triphenylmethylhexafluorophosphate (0.69 g, 1.8 mmol) in dichloromethane at room temperature was added a rotational isomer of 1,1,2,2-tetrakis (2',6'-dimethoxyphenyl)ethane (0.90 g, 1.5 mmol). After stirring for 18 hours, water (10 mL) was added and the resulting mixture was extracted with dichloromethane and dried over anhydrous magnesium sulfate. Filtration and removal of the solvent gave tetrakis(2,6-dimethoxyphenyl) ethylene after washing with diethyl ether. {Note: Only one of the rotational isomers gives (5) upon treatment with trityl cation.}

E. 2,2',2",2'",6,6',6",6'"-octahydroxytetraphenylethylene [tetrakis(2,6-dihydroxyphenyl)ethylene] (6)

A solution of tetrakis(2,6-dimethoxyphenyl)ethylene (0.45 g, 0.8 mmol) in dichloromethane cooled to −78° C. was treated with boron tribromide (1.0 mL, 10 mmol). The resulting solution was warmed to room temperature and stirred for 16 hours, after which the reaction mixture was poured into ice-cold saturated aqueous sodium bicarbonate.

This mixture was extracted with ethyl acetate and the combined extracts dried over anhydrous magnesium sulfate. Removal of the solvent and washing with diethyl ether gave 2,2',2",2'",6,6',6",6'"-octahydroxytetraphenylethylene.

EXAMPLE 6

New Derivatives of the 2,2',2",2'"-tetrahydroxytetraphenylethylene

A. 2,2',2",2'"-tetra(allyloxy)tetraphenylethylene (8)

A solution of 2,2',2",2'"-tetrahydroxytetraphenylethylene (7) (0.110 g, 0.277 mmol) and potassium carbonate (0.762 g, 5.51 mmol) in 8.5 mL of acetone was heated to reflux for 16 hours under a nitrogen atmosphere. After removal of the volatiles in vacuo, the residue was redissolved in 50 mL of water and extracted with 50 mL of dichloromethane. The organic layer was washed with water and brine and then dried over sodium sulfate, filtered, and the solvent was evaporated. The residue was recrystallized from dichloromethane-diethyl ether to give 2,2',2",2'"-tetra(allyloxy)tetraphenylethylene.

B. 2,2',2",2'"-tetrahydroxy-3,3',3",3'"-tetra(allyl)tetraphenylethylene (9)

A solution of 2,2',2",2'"-tetra(allyloxy)tetraphenylethylene (8) (0.085 g, 0.153 mmol) in 2 mL of mesitylene was degassed in a thick-walled glass vessel fitted with a teflon high vacuum stopcock. After backfilling with nitrogen, the vessel was sealed and heated to 200° C. for 14 hours. After removing the solvent under vacuum, a white solid was obtained from the oily residue by addition of hexanes and ultrasonification. After removal of volatiles, the nearly pure 2,2',2",2'"-tetrahydroxy-3,3',3",3'"-tetra(allyl)tetraphenylethylene (9) was obtained in quantitative yield and was used without further purification.

C. 2,2',2",2'"-tetrahydroxy-3,3',3",3'"-tetra(n-propyl)tetraphenyl ethylene (10)

A solution of 2,2',2",2'"-tetrahydroxy-3,3',3",3'"-tetra(allyl)tetraphenylethylene (9) (0.020 g, 0.0359 mmol) in 2 mL of methanol was maintained under 300 psig of hydrogen in the presence of 10% Pd—C catalyst (0.003 g, 0.0028 mmol) for 4 hours at room temperature. After filtration through celite and removal of the volatiles, 2,2',2",2'"-tetrahydroxy-3,3',3",3'"-tetra(n-propyl)tetraphenylethylene (10) was isolated as a white solid in quantitative yield.

D. 2-hydroxy-2'-methoxybenzophenone (12)

This procedure is based on that reported in Tetrahedron Lett., 1966, 4153. To a solution of 2,2'-dimethoxybenzophenone (11) (6.7 g, 0.0277 mol) in anhydrous dichloromethane (95 mL) cooled to −65° C. under nitrogen was added 52 mL of a 1.0 M solution of boron trichloride in heptane (0.052 mol). The mixture was allowed to warm to room temperature and stirred for 75 minutes. The reaction mixture was slowly poured into a cold (0° C.) solution of saturated aqueous sodium bicarbonate, which was then extracted with dichloromethane. The organic extracts were washed with water and saturated with NaCl, followed by drying over anhydrous sodium sulfate. Analytically pure product was obtained after removal of the solvent in quantitative yield.

E. 2-benzyloxy-2'-methoxybenzophenone (13)

A mixture of 2-hydroxy-2'-methoxybenzophenone (12) (8.08 g, 0.0354 mol), potassium carbonate (24.5 g, 0.177 mol) and benzyl bromide (4.4 mL, 0.037 mol) in 90 mL of dimethylsulfoxide was stirred overnight at room temperature. The resulting reaction mixture was diluted with diethyl ether and water and the aqueous layer was extracted with fresh diethyl ether. The combined organic layers were washed with water, followed by saturated NaCl and dried over sodium sulfate. After purification by flash column chromatography (silica gel, dichloromethane/hexanes eluent), 2-benzyloxy-2'-methoxybenzophenone (13) was obtained as a colorless oil.

F. 2-benzyloxy-2'-methoxybenzophenone hydrazone (14)

A stirred suspension 2-benzyloxy-2'-methoxybenzophenone (13) (7.98 g, 0.025 mol) in hydrazine monohydrate (16 mL, 0.328 mol) and 1-butanol (25 mL) was heated to reflux overnight. After cooling to room temperature, the reaction mixture was poured into water saturated with salt and diluted with tetrahydrofuran. The organic phase which forms was separated, washed with water, saturated salt, and evaporated to dryness by rotary evaporation followed by application of high vacuum and mild heating. The resulting oil, 2-benzyloxy-2'-methoxybenzophenone hydrazone (14), which sometimes solidifies, still contains n-butanol and was used without further purification.

G. E and Z—1,2-di(2'-benzyloxyphenyl)-1,2-di(2'-methoxyphenyl)ethane (15)

To a solution of 2-benzyloxy-2'-methoxybenzophenone hydrazone (14) (2.246 g, 6.76 mmol) in anhydrous acetonitrile (80 mL) cooled to 0° C. in an ice-salt bath and protected form ambient light using aluminum foil, was added nickel peroxide (5.5 g, excess, prepared as described in J. Org. Chem., 1962, 27, 1597) in one portion. The mixture was stirred for 1 hour at 0° C. and then filtered through basic alumina (Activity I) to remove the nickel residues. After rinsing the alumina with additional acetonitrile (80 mL), the intense pink-red filtrate was cooled to 0° C. and treated with a few drops of a benzene solution of anhydrous p-toluenesulfonic acid (prepared from 3.6 g anhydrous p-toluenesulfonic acid in 39 mL anhydrous benzene). The color immediately changed to yellow-brown. The acid was neutralized by the addition of a few drops of concentrated aqueous potassium hydroxide and the volatiles removed under reduced pressure. The residue was purified by flash chromatography on silica gel (dichloromethane/hexanes eluent) to give a mixture of E and Z—1,2-di(2'-benzyloxyphenyl)-1,2-di (2'-methoxyphenyl)ethane (15) as a white solid.

H. E and Z—1,2-di(2'-hydroxyphenyl)-1,2-di(2'-methoxyphenyl)ethylene (16)

A solution of E and Z—1,2-di(2'-benzyloxyphenyl)-1,2-di(2'-methoxyphenyl)ethane (15) (0.020 g, 0.033 mmol) and 10% palladium on carbon (0.002 g, 0.002 mmol) in ethyl acetate (0.4 mL) and methanol (1.5 mL) was pressurized under hydrogen (610 psig) at room temperature for 18 hours. The resulting mixture was filtered through celite and the volatiles removed under reduced pressure. The oily solid that results solidifies to a white solid mixture of separable E and Z—1,2-di(2'-hydroxyphenyl)-1,2-di (2'-methoxyphenyl)ethylene (16) after ultrasonification in hexanes and is isolated in quantitative yield.

What is claimed is:

1. A process for producing a 2,2',2",2'" tetra hydroxy tetraphenylethylene comprising:
   (i) reacting to 2,2' di $C_{1-6}$ alkoxybenzophenone with hydrazine monohydrate to produce a 2,2'di-$C_{1-6}$ alkoxybenzophenone hydrazone;
   (ii) oxidizing the 2,2'di $C_{1-6}$ alkoxybenzophenone hydrazone in the presence of nickel peroxide and the absence of light at a temperature of not more than 0° C. to yield the diazo derivative of 2,2'di-$C_{1-6}$ alkoxybenzophenone hydrazone;
   (iii) in the absence of light and at a temperature of not more than 25° C. decomposing the diazo derivative of 2,2'di-$C_{1-6}$ alkoxybenzophenone hydrazone with anhydrous p-toluene sulphonic acid; to yield the 2,2',2",2"' tetra $C_{1-6}$ alkoxy tetrapenyl ethylene; and (iv) dealkylating the resulting 2,2',2",2"' tetra $C_{1-6}$ alkoxy tetraphenyl ethylene to form the 2,2',2",2"' tetrahydroxy tetraphenyl ethylene.

2. The process according to claim 1, wherein the dealkylation is by reaction with boron tribromide.

3. A process according to claim 2, for preparing 2,2',2",2"'-(tetrahydroxy)tetraphenylethylene comprising dealkylating 2,2', 2",2"'-(tetramethoxy)tetraphenylethylene with boron tribromide.

4. The process according to claim 1, further comprising reacting the resulting 2,2',2"2"'-(tetrahydroxy) tetraphenylethylene with an anhydride of a $C_{1-6}$ carboxylic acid.

5. The process according to claim 4, for preparing 2,2',2",2"'-(tetraacetoxy)tetraphenylethylene comprising reacting 2,2',2",2"'-(tetrahydroxy)tetraphenylethylene with anhydrous acetic anhydride.

6. The process according to claim 1, further comprising reacting the resulting 2,2'2",2'"-(tetrahydroxy) tetraphenylethylene with trifluoromethanesulfonic anhydride.

7. A process according to claim 6, for preparing 2,2',2",2'"-tetrakis(trifluoromethylsulfonyloxy)tetraphenylethylene comprising reacting 2,2',2",2'"-(tetrahydroxy) tetraphenylethylene with trifluoromethanesulphonic anhydride.

8. The process according to claim 2, further comprising reacting 2,2',2",2"'-tetrahydroxyphenylethylene with a $C_{3-6}$ allylating agent.

9. The process according to claim 8, wherein the $C_{3-6}$ allylating agent is a 1-bromo $C_{3-6}$ allyl compound.

10. The process according to claim 9, further comprising subjecting the resulting 2,2',2",2"'-tetra $C_{3-6}$ allyloxy tetraphenylethylene to a Claisen rearrangement resulting in a 2,2',2",2"'-tetrahydroxy-3,3',3",3"'-tetra $C_{3-6}$ allyl tetraphenylethylene.

11. The process according to claim 10, further comprising hydrogenating the 2,2',2",2"'-tetrahydroxy-3,3',3",3"'-tetra $C_{3-6}$ allyl tetraphenylethylene to yield a 2,2',2",2"'-tetrahydroxy-3,3',3",3"'-tetra $C_{3-6}$ alkyl tetraphenylethylene.

12. The process according to claim 9, wherein the allylating agent is allylbromide.

* * * * *